United States Patent [19]
Yamaguchi et al.

[11] Patent Number: 4,997,819
[45] Date of Patent: Mar. 5, 1991

[54] FATTY EMULSION STABILIZED BY A POLYSACCHARIDE DERIVATIVE

[75] Inventors: Shigehiko Yamaguchi, Nagasaki; Junzo Sunamoto, Kusatsu, both of Japan

[73] Assignee: Nippon Oil & Fats Co., Ltd., Tokyo, Japan

[21] Appl. No.: 439,810

[22] Filed: Nov. 21, 1989

[30] Foreign Application Priority Data

Nov. 25, 1988 [JP] Japan .................. 63-296018

[51] Int. Cl.$^5$ .................. A61K 31/00; C08B 31/00; C08B 35/00; C08B 37/00
[52] U.S. Cl. .................. 514/54; 514/937; 514/938; 514/943; 536/102; 536/103
[58] Field of Search .................. 514/54, 937, 938, 943; 426/602, 601; 436/71; 536/102, 103

[56] References Cited

U.S. PATENT DOCUMENTS 4,293,572 10/1981 Silva et al. .................. 426/602
4,312,891 1/1982 Eisfeldt .................. 426/582
4,461,777 7/1984 Murase et al. .................. 426/602

*Primary Examiner*—Ronald W. Griffin
*Assistant Examiner*—Everett White
*Attorney, Agent, or Firm*—Antonelli, Terry, Stout & Kraus

[57] ABSTRACT

The invention is a fatty emulsion stabilized by a polysaccharide derivative, wherein the fatty emulsion contains a polysaccharide derivative which is substituted by a fatty acid or cholesterol at a proportion of 0.5–5 per 100 of sugar units.

4 Claims, 5 Drawing Sheets

1 μm

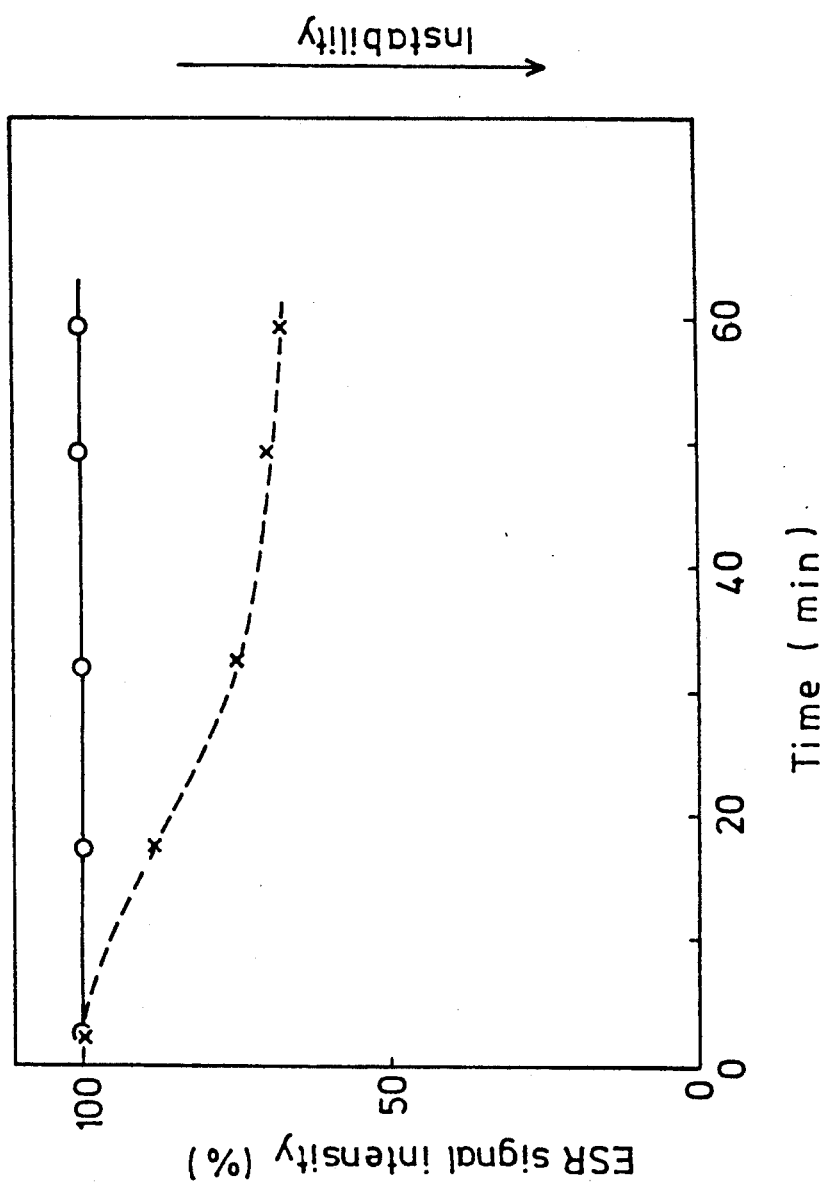

FATTY EMULSION STABILIZED BY A POLYSACCHARIDE DERIVATIVE

BACKGROUND OF THE INVENTION

The present invention relates to emulsions used for medicine, food and the like, more particularly to fatty emulsions stabilized by polysaccharide derivatives which can embed fat-soluble substances in large quantities.

As medicine carriers, albumin, fibrinogen, erthrocyte ghost, gelatin, starch, polylactide, polyglycoride, dextran, polyethyl carbonate, liposome, emulsions and the like have been found. In these materials, liposome and O/W emulsions are hopeful.

It is well-known that, when the surface of liposome is coated with a polysaccharide derivative by their mutual interaction of non-covalent bonds, the structure of liposome is stabilized. (Japanese Laid-Open Patent Publication Nos. 58-49311 and 61-69801).

Lately, as mentioned above, liposome and O/W emulsions are hopeful as medicine carriers. Among them, liposome has disadvantages which are the lack of chemical and mechanical stabilities and the difficulty of long-term preservation. The present inventors found that the structure stability of liposome was considerably improved by coating the surface of liposome with a polysaccharide. However, a satisfactory stability is not yet obtained. The other hand, an O/W emulsion comprising of lecithin, oil and water is excellent as a carrier of fat-soluble medicines because it is possible to embed them in large quantities. Furthermore, fatty emulsions (lipid microsphere) has been conventionally prepared by emulsifying oil with phospholipids of negative electric charge for obtaining the colloid stability. When the surface electric charge of particles is neutralized by the presence of calcium ions and the like, the embedding of fat-soluble medicines, the pH change in the system, etc., these fatty emulsions tend to associate or aggregate. Accordingly, there are problems in regard of the colloid stability.

The present inventors have conducted research for resolving the above problems and for stably emulsifying oil with emulsions other than phospholipids and they have found that oil is stably emulsified by using polysaccharide derivatives which can efficiently improve the structure stability of liposome. Then, they have found fatty emulsions stabilized by polysaccharide derivatives.

SUMMARY OF THE INVENTION

An object of the present invention is to provide colloid-chemically and biochemically stable fatty emulsions which can embed and maintain fat-soluble materials in large quantities.

The present invention provides a fatty emulsion stabilized by a polysaccharide derivative characterized in that the fatty emulsion contains a polysaccharide derivative which is substituted by a fatty acid or cholesterol at a proportion of 0.5 to 5 per 100 sugar units.

BRIEF EXPLANATION OF THE DRAWINGS

FIG. 5 shows ESR signal intensities that the stability of the product obtained in Example 2 are compared with the stability of the commercially available product in the presence of $CaCl_2$.

In FIGS. 4 and 5, o shows the result obtained by using five emulsions of the present invention and x shows the result obtained by using a commercially available lipid microsphere.

DETAILED DESCRIPTION OF THE INVENTION

Figure 1:
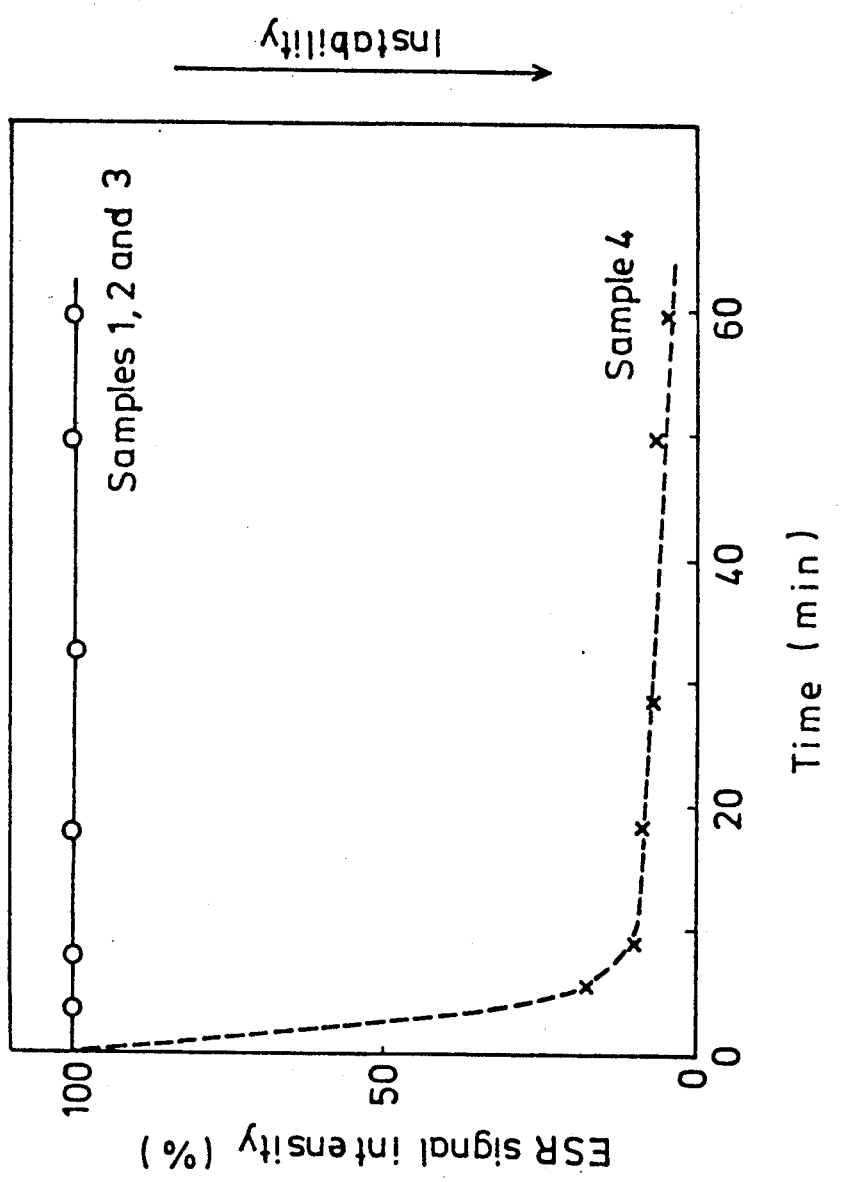
FIG. 1 is a figure of ESR signal intensities showing the stability of the emulsions obtained in Example 1.

The polysaccharide derivative to be used in accordance with the present invention can be obtained from natural or synthetic products.

As the polysaccharide which constitutes the polysaccharide derivative, pullulan, amylopectin, amylose, dextrin, cyclodextrin, dextran, hydroxyethyldextran, mannan or the like can be exemplified.

The polysaccharide derivative is a compound in which the hydroxy groups of the polysaccharide are substituted by a fatty acid or cholesterol at a proportion of 0.5 to five per 100 of sugar units. When the proportion is less than 0.5, a stable fatty emulsion can not be obtained. When the proportion is more than 5, it is difficult to synthesize the polysaccharide derivative.

The polysaccharide derivative preferred in particular is a compound in which the hydroxy groups of carbons situated in 6- or 3-positions of the sugar skeleton are substituted by $-OCH_2CONHCH_2CH_2NHR$ wherein R is H or a cholesteryloxycarbonyl group, and the hydroxy groups are substituted by the above formulas wherein R is a cholesteryloxycarbonyl group at a proportion of 0.5 to three per 100 of sugar units.

Furthermore, the polysaccharide derivative to be used in accordance with the present invention is preferably on ester which is derived from a saccharide and a fatty acid such as, for example stearic acid, palmitic acid, myristic acid or lauric acid.

For bonding a cholesterol to a polysaccharide directly, for example, ethylenediamine is used as a spacer in considering of steric hindrance of the cholesterol and the polysaccharide. Firstly, primary hydroxy groups (in 6-position) of the polysaccharide having high reactivities are carboxymethylated under alkali conditions. Then, the obtained compound and ethylenediamine are reacted with a condensation agent (EDC, 1-ethyl-3-(3-dimethylaminopropyl)carboxyimide to obtain amide bonds. Finally, the obtained amide and cholesteryl chloroformate are reacted in an anhydrous system to introduce cholesterol groups in the polysaccharide.

The fatty emulsion of the present invention can contain water and oil in addition to the above polysaccharide derivative. As oil to be used, fish oil, vegetable oil, such as soy bean oil, sesame oil, rape oil, palm oil and cottonseed oil, fatty acids, fatty esters, middle length chain fatty acid triglycerides and these mixture can be exemplified.

The ratio of the polysaccharide derivative of the present invention and the oil is preferably 0.1 to 1.0 (wt/wt) so as to form a stable emulsion. As water, pure water such as distilled water for injection and sterilized water, glucose liquid and physiological sodium chloride solution can be used.

The concentration of the fatty emulsion of the present invention is preferably high. However, when the concentration is too high, the density and the viscosity become too high. Practically, the ratio of oil/water is 0.01-0.5 (wt/wt).

The fatty emulsion of the present invention can dissolve fat-soluble anticancer agents, fat-soluble compounds such as antibiotics, steroid hormones and prostaglandins in large quantities in the oil phase and it can be used as a solubilizer of these fat-soluble substances. Accordingly, when the fatty emulsion of the present invention is used as a medicine carrier, it can be given by the use of an intraveneous injection, an intraarterial injection or an intralymphangial injection, or directly to a disease part.

Namely, the polysaccharide derivative to be used in accordance with the present invention contributes to improve the stability of colloidal chemical structure of oil drops and to develop the cell specificity required to targetting treatments and shows ideal properties as the medicine carrier.

The sugar chains are concerned in the mechanism of information transmission in vivo. By changing the kind of the polysaccharide which constitutes the polysaccharide derivative to be used in accordance with the present invention, for example, by introducing a sialic acid residue or an amino sugar chain, or by phosphorizing the sugar chains, the cell recognition properties of the oil drops themselves which are coated with the polysaccharide can be artificially changed. By binding antibody to the polysaccharide derivative, an emulsion possible to target the aimed part by the antigen-antibody reaction can be prepared.

For preparing the emulsion of the present invention, various homogenizers such as a Manton-Gory type homogenizer and the like and an ultrasonic generator of high output power can be used. For controlling the particle diameters of the oil drips after the emulsification, gel filtration or ultracentrifugation can be conducted.

The emulsion of the present invention principally comprises of oil and water in addition to the polysaccharide derivative. Furthermore, isotonic agents such as glycerin, various surfactants as emulsifying auxiliary agents and anti-oxidizing agents for oil can be added to the emulsion.

According to the present invention, fat-soluble materials can be emulsified in water or solubilized by homogeneously dispersion. Especially, the fat-soluble medicines can be solubilized in large quantities and targetting treatments can be conducted. As a result, medical lipid microspheres which are ideal for the fat-soluble medicines can be provided. The fatty emulsion can be used as a carrier for the fat-soluble medicines and can be broadly used in fields of food chemistry and the other industry.

DESCRIPTION OF PREFERRED EMBODIMENTS

The following Examples illustrate the present invention more specifically.

SYNTHESIS EXAMPLE 1

Synthesis of carboxymethylated pullulan

Pullulan (average molecular weight 50,000) 3.0 g (1.9 $\times 10^{-2}$ mole monosaccharide units) was charged in a 200 ml flask of an eggplant type and an aqueous solution 74 ml of 1.35M sodium monochloroacetate was added to dissolve thoroughly the pullulan. An aqueous solution 10 ml of 10N sodium hydroxide was added with stirring on a magnetic stirrer and 16 ml of distilled water was added. The obtained solution contained 1M sodium monochloroacetate and 1N sodium hydroxide. The solution was allowed to react for seven hours at 25° C. with stirring. (Carboxy methyl groups at a proportion of about 10 per 100 g of monosaccharide units were introduced).

Then, an aqueous solution 20 ml of 1M sodium dihydrogen phosphate ($1.0 \times 10^{-2}$ moles) was added to the reacted solution. The reaction was stopped at pH 7 by adding an aqueous solution of 6N hydrochloric acid and an aqueous solution of 1N hydrochloric acid. The obtained solution was transferred to a dialysis tube and dialyzed against distilled water. The dialysis was continued with 1 liter $\times 15$ changes of distilled water. The absence of free monochloroacetic acid was confirmed by UV measurement after concentrating the dialyzed outer liquid to about one-hundredth. Yield: 2.96 g ($1.8 \times 10^{-2}$ mole monosaccharide units).

Syntheses of N-(2-aminoethyl)carbamoylmethylated pullulan

Carboxymethylated pullulan 2.9 g ($1.8 \times 10^{-2}$ mole monosaccharide units) obtained as described in the above was charged in a 200 ml flask of an eggplant type and 40 ml of distilled water was added to dissolve throughly carboxymethylated pullulan. Then, an aqueous solution of 0.1N sodium hydroxide and an aqueous solution of 0.1N hydrochloric acid were added with stirring on a magnetic stirrer to obtain a solution of pH 4.7. Further, ethylenediamine dihydrochloride 1.6 g ($1.2 \times 10^{-2}$ mole) was added and EDC hydrochloride 2.3 g ($1.2 \times 10^{-2}$ mole) which was divided into three groups was added at 10 minutes intervals to adjust the pH value of the solution to pH 4.7. The mole ratio of the solutes in the reaction system was carboxymethylated pullulan:ethylenediamine:EDC=3:2:2.

The mixed solution was allowed to react for seven hours at 25° C. with stirring while maintaining at pH 4.7. (N-(2-Aminoethyl)carbamoylmethyl groups at a proportion of about 3 per 100 of monosaccharide units were introduced). Then, the reacted solution was transferred to a dialysis tube and dialyzed against distilled water. The dialysis was continued with 1 liter $\times 15$ changes of distilled water. The absence of free ethylenediamine was confirmed by a ninhydrin reaction after concentrating the dialyzed outer liquid to about one-hundredth. Yield: 2.81 g ($1.7 \times 10^{-2}$ mole monosaccharide units).

Synthesis of N-[2-(cholesteryloxycarbonylamino)ethyl]carbamoylmethylated pullulan N-(2-Aminoethyl)carbamoylmethylated pullulan 2.7 1 g ($1.7 \times 10^{-2}$ mole monosaccharide units) was charged in a 100 ml flask of an eggplant type equipped with a reflux condenser which was sealed with a calcium chloride tube and anhydrous dimethyl sulfoxide 30 ml was added with stirring on a magnetic stirrer to dissolve throughly N-(2-aminoethyl)carbamoylmethylated pullulan. Then, anhydrous pyridine 2 ml was added and the flask was heated at 60°-70° C. in an oil bath.

The other hand, cholesteryl chloroformate 0.77 g ($1.7 \times 10^{-3}$ mole) was charged in sample bottle and anhydrous dimethylformamide 5 ml was added. The mixture was heated and cholesteryl chloroformate was throughly dissolved. The obtained cholesteryl chloroformate solution was added to the above N-(2-aminoethyl)carbamoylmethylated pullulan solution. The mole ratio of the solutes in the reaction system was N-(2-aminoethyl)carbamoylmethylated pullulan:cholesteryl chloroformate=10:1.

The mixed solution was allowed to react for seven hours at 60°-70° C. with stirring. Then, the hot solution was added dropwise to ethanol 200 ml to precipitate a polysaccharide. The polysaccharide obtained by filtration was dissolved in distilled water 100 ml. The obtained solution was dialyzed against distilled water. The dialysis was continued with 1 liter×10 changes of distilled water. Then, impurities (e.g. fibers of filter paper) was removed by filtration and the filtrate was lyophilized. Yield: 2.03 g ($1.3\times10^{-2}$ mole monosaccharide units). The amount of the introduced cholesterol per 100 monosaccharide units was calculated from a proton integral ratio of polysaccharide and cholesterol which are obtained by $^1$H-NMR measurement.

Using the above process, the final product CHP-50-1.9 was obtained. (CHP: cholesterol-modified pullulan, 50: average molecular weight (MW=50,000), 1.9: the numbers of the substituted cholesterol per 100 monosaccharide units).

EXAMPLE 1

Changing the ratio of the obtained polysaccharide derivative (CHP-50-1.9) and oil (a middle length chain triglyceride: Panasate 800 produced by Nippon Oil & Fats CO., Ltd.), fatty emulsions of Samples 1, 2 and 3 were prepared. In the process for emulsifying, using a probe type sonicator (200 W, Model UR-200P, manufactured by Tommy Company in Japan), the samples were prepared by ultrasonic treatment at 70° C. for 15 minutes in a stream of $N_2$.

Polysaccharide derivative (CHP-50-1.9) used in the experiments is the pullulan cholesterol derivative obtained the above Synthesis Example and the molecular weight of pullulan was 50,000 and the numbers of the substituted cholesterol was 1.9 per 100 of monosaccharide units.

For comparison, an emulsion of Sample 4 was prepared by using the same method as in the above method from a non-treated pullulan.

The emulsified conditions of the obtained emulsion were firstly estimated with the naked eye. The results are shown in Table 1. The emulsified conditions of Samples 1,2 and 3 are good.

TABLE 1

| Sample | CHP-50-1.9 /mg | Panasate 800/mg | Glycerin /mg | Water /ml | Emulsified conditions |
|---|---|---|---|---|---|
| 1 | 10 | 20 | 25 | 1 | o |
| 2 | 20 | 100 | 25 | 1 | o |
| 3 | 50 | 100 | 25 | 1 | o |
| 4 | *10 | 20 | 25 | 1 | x |

*Non-treated Pullulan
o Good emulsified condition (homogeneous white turbidity condition)
x No Good. Small liberated and phase-separated oil drops floated on the emulsified liquid surface.

ESTIMATION OF STABILITY OF THE EMULSIFIED LIQUID BY ESR METHOD

To the emulsified liquid 3 ml of Sample 3 in Table 1, 12-NS(methyl 12-doxylstearate 4.3 μg) of an ESR probe was added. The probe was solubilized by ultrasonic treatment at 70° C. for 2 minutes in a stream of $N_2$.

When the emulsified liquid was unstable, oil drops condensed or fused, and the water phase and the oil phase separated. Since the above 12-NS was dissolved in the oil phase only, when the emulsified liquid was stable, the 12NS was homogemeously dispersed in the emulsified liquid and the ESR signal strength was always kept constant. However, when the oil phase and the water phase were separated, the oil phase having small specific gravity floated on the surface of the solution in a tube for the ESR measurement and the ESR signal strength lowered. By using the above phenomena, the ESR signal strength of the 12-NS was measured every given period of time and the colloidal stability of the emulsified liquid was estimated.

By using the ESR method, the stability of Samples 1,2,3 and 4 in Table 1 was compared. The results are shown in FIG. 1. As shown in FIG. 1, when the ratio of polysaccharide derivative/oil (wt/wt) is 0.1 or more, the stable emulsions are obtained.

OBSERVATION UNDER AN ELECTRON MICROSCOPE

Sample 3 in Table 1 was observed under a transmission electron microscope (JEM-100SX, JEOL, X25,000). After the sample was dyed with uranyl acetate, it was fixed on a copper mesh coated with a collodion-carbon film and observed.

Figure 2:
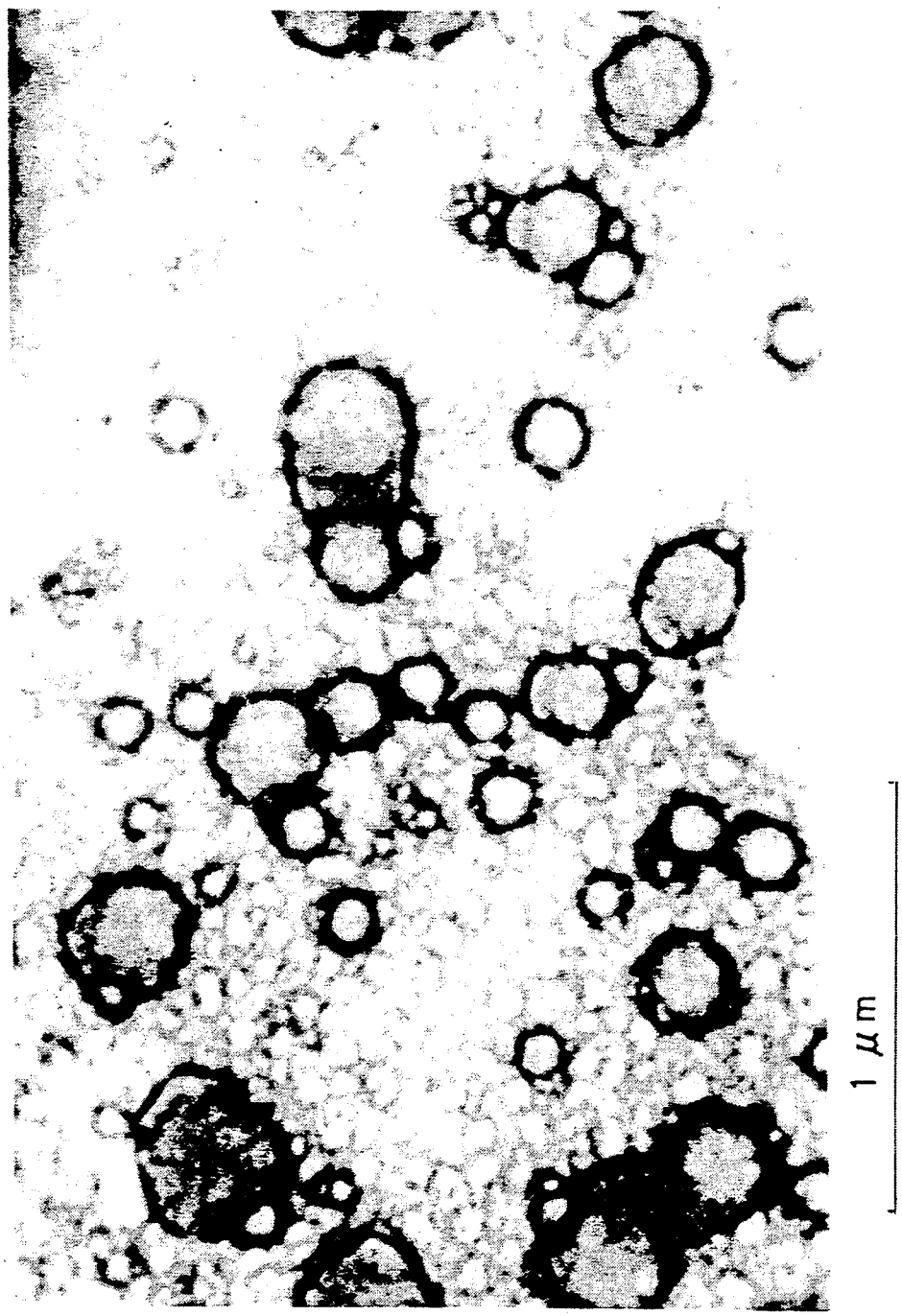
FIG. 2 is a transmission electron microscope photograph in which the particle structure of the emulsion of Sample 3 in Example 1 is shown.

In FIG. 2, a transmission electron microscope photograph of the sample is shown. Oil drops having a particle diameter of 0.5 μm and less can be observed. Furthermore, the sample was observed under a scanning electron microscope (JSM-T100, JEOL, X7500). After the sample was adsorbed on a filter paper (Wattman NO. 2), it was dyed with a glutaraldehyde/marachite green liquid and fixed with osmium tetraoxide. Then the sample was deposited with gold and observed. Oil drops having a particle diameter of 0.5 μm and less can be observed.

MEASUREMENT OF GRAIN SIZE DISTRIBUTION

Figure 3:
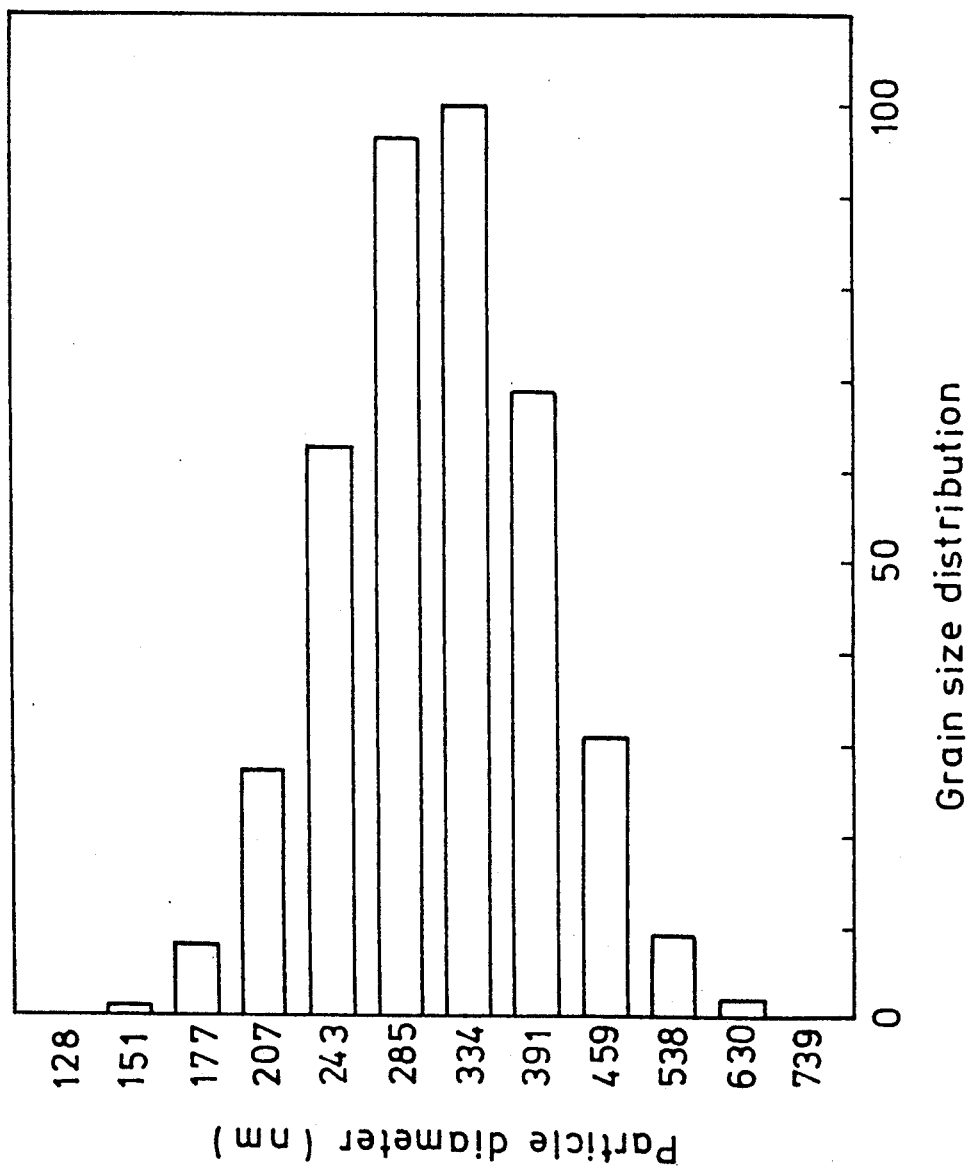
FIG. 3 shows grain size distribution of Sample 3 in Example 1.

The grain size distribution of Sample 3 in Table 1 was measured with a device for measuring grain size distribution (NICOMP 370HPL, Pacific Science Company). The results are shown in FIG. 3. In this experiment, it was found that the prepared emulsion had an average particle diameter of 0.3 μm and that the particle size was normally distributed.

EXAMPLE 2

Using the same constituents as used in Sample 3 of Example 1 except that the CHP-50-1.9 was changed to several polysaccharide derivatives, emulsions were prepared. The stability of these emulsions was observed with the naked eye.

The same emulsifying method as in Example 1 was used.

Five kinds of polysaccharide derivatives are used: OPA-112-2.8 (amylopectin having a molecular weight of 112,000 and the substituted palmitic acid 2.8 per 100 of monosaccharide units), OPD-176-1.5 (dextran having a molecular weight of 176,000 and substituted palmitic acid 1.5 per 100 of monosaccharide units), CHAp-112-2.0 (amylopectin having a molecular weight of 112,000 and the substituted cholesterol 2.0 per 100 of monosaccharide units), CHD-176-1.7 (dextran having a molecular weight of 176,000 and the substituted cholesterol 1.7 per 100 of monosaccharide units) and CHP-50-1.9 (pullulan having a molecular weight of 50,000 and the substituted cholesterol 1.9 per 100 of monosaccharide units).

The results are shown in Table 2. Stable emulsions were obtained without depending on the kinds of polysaccharides.

TABLE 2

| Sample | Polysaccharide derivatives | Emulsified Conditions | |
|---|---|---|---|
| | | After the preparation | One month after* |
| 1 | OPA-112-2.8 | o | o |
| 2 | OPD-176-1.5 | o | o |
| 3 | CHAp-112-2.0 | o | o |
| 4 | CHD-176-1.7 | o | o |
| 5 | CHO-50-1.9 | o | o |

*Kept at 4° C. in an atmosphere of air
o Good emulsified condition (homogemeously white turbidity condition)

EXAMPLE 3

Using the same constituents and conditions as used in Sample 3 of Example 1 except that Panasate 800 was changed to several kinds of oil, emulsions were prepared. The stability of these emulsions was observed with the naked eye.

The same emulsifying method as in Example 1 was used. The results are shown in Table 3. Stable emulsions were obtained without depending on the kinds of oil.

TABLE 3

| Sample | Oil | Emulsified Conditions | |
|---|---|---|---|
| | | After the preparation | One month after* |
| 1 | Panasate 800 | o | o |
| 2 | Soy bean oil | o | o |
| 3 | Fish oil | o | o |
| 4 | Perilla oil | o | o |
| 5 | α-Linolenic acid | o | o |

*Kept at 4° C. in an atmosphere of air
o Good emulsified condition (homogemeously white turbidity condition)

EXAMPLE 4

The 12-NS was embed as an probe. The stability of the emulsions of the present invention and the stability of a commercially available lipid microsphere were compared by the ESR method.

Figure 4:
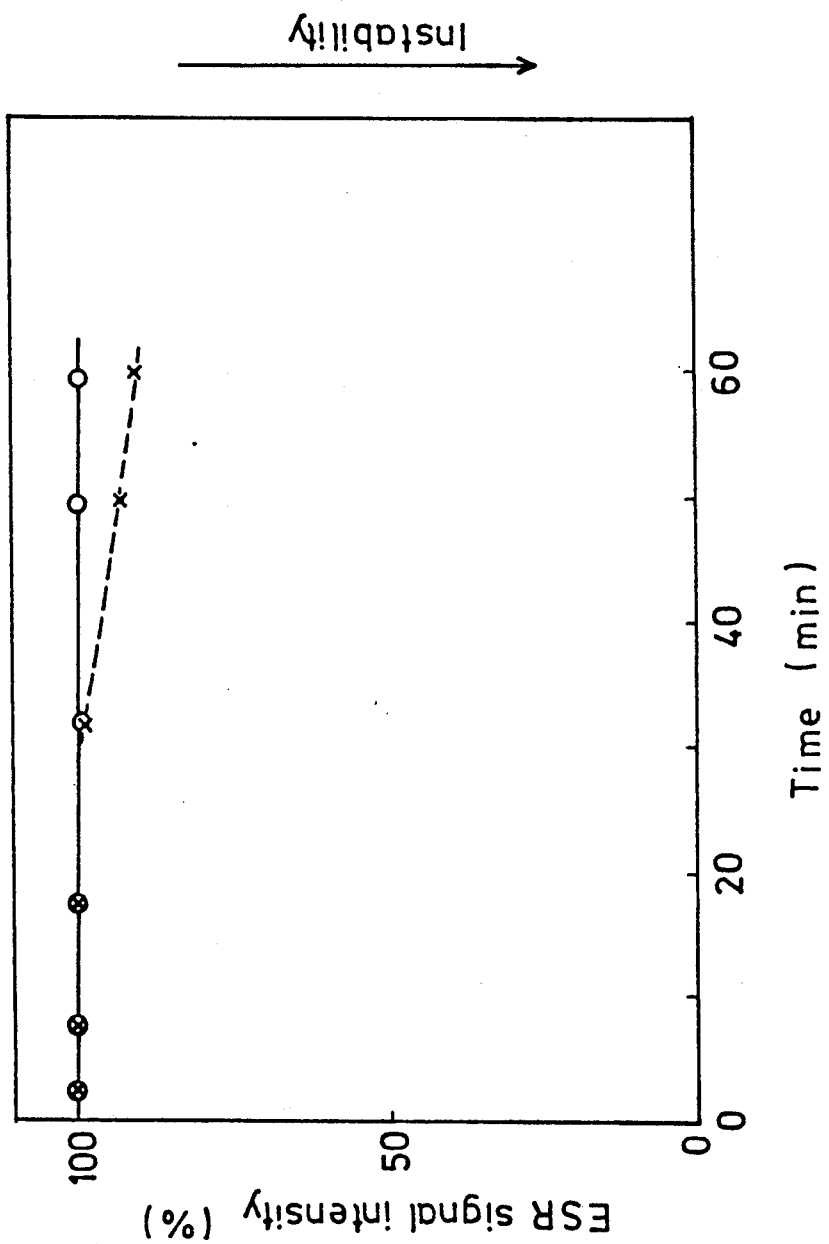
FIG. 4 shows ESR signal intensities that the stability of the product obtained in Example 2 are compared with the stability of the commercially available product.

Five emulsions of the present invention were prepared by the same method as in Example 2. The results are shown in FIG. 4. When the 12-NS was added as a probe, the commercially available lipid microsphere became unstable and the phases were immediately separated. In contrast, all of the emulsions of the present invention were stable.

EXAMPLE 5

When the emulsions of the present invention were injected in a blood vessel, the stability of emulsions to Ca (II) ion under physiological conditions should be considered. The stability of the emulsions of the present invention and the stability of a commercially available lipid microsphere were compared in the presence of $CaCl_2$ by the same ESR method as in Example 4.

Five emulsions of the present invention were prepared by the same method as in Example 2. The results in the presence of $CaCl_2$ (5 mM) are shown in FIG. 5. The commercially available lipid microsphere became unstable in the presence of $CaCl_2$ (5 mM) and the phases were easily separated. On the other hand, all of the emulsions of the present invention was very stable in spite of the presence $CaCl_2$.

We claim:

1. A fatty emulsion stabilized by a polysaccharide derivative, wherein the fatty emulsion contains a polysaccharide derivative which is substituted by cholesterol at a proportion of 0.5–5 per 100 of sugar units.

2. A fatty emulsion as claimed in claim 1 in which the polysaccharide derivative is a pullulan, an amylopectin or or a dextrin.

3. A fatty emulsion stabilized by a polysaccharide derivative, wherein the fatty emulsion contains a polysaccharide derivative which is N-[2-(cholesteryloxy-carbonylamino)ethyl]carbamoylmethylated pullulan.

4. A fatty emulsion stabilized by a polysaccharide derivative, wherein the fatty emulsion contains a polysaccharide derivative which is substituted by cholesterol at a proportion of 0.5–5 per 100 of sugar units and which is N-[2-(cholesteryloxy-carbonylamino)ethyl]-carbamoylmethylated pullulan.

* * * * *